(12) United States Patent
Lee et al.

(10) Patent No.: US 9,447,211 B2
(45) Date of Patent: Sep. 20, 2016

(54) PREPARATION METHOD OF CATALYST FOR POLYOLEFIN POLYMERIZATION AND PREPARATION METHOD OF POLYOLEFIN

(71) Applicant: LG CHEM, LTD., Seoul (KR)

(72) Inventors: Yong Ho Lee, Daejeon (KR); Ki Soo Lee, Daejeon (KR); Eun Kyoung Song, Daejeon (KR); Heon Yong Kwon, Daejeon (KR); Min Seok Cho, Daejeon (KR); Dae Sik Hong, Daejeon (KR); Man-Seong Jeon, Daejeon (KR); Kyoung-Chan Lim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 119 days.

(21) Appl. No.: 14/390,727

(22) PCT Filed: May 8, 2013

(86) PCT No.: PCT/KR2013/003996
§ 371 (c)(1),
(2) Date: Oct. 3, 2014

(87) PCT Pub. No.: WO2014/175495
PCT Pub. Date: Oct. 30, 2014

(65) Prior Publication Data
US 2016/0152742 A1 Jun. 2, 2016

(30) Foreign Application Priority Data
Apr. 23, 2013 (KR) .................. 10-2013-0045011

(51) Int. Cl.
| | | |
|---|---|---|
| C08F 4/633 | (2006.01) |
| C08F 4/635 | (2006.01) |
| C08F 4/69 | (2006.01) |
| C08F 4/6592 | (2006.01) |
| C08F 210/16 | (2006.01) |
| C08F 110/02 | (2006.01) |
| C07C 2/06 | (2006.01) |
| C07C 2/32 | (2006.01) |
| C08F 4/622 | (2006.01) |
| C08F 4/02 | (2006.01) |
| C08F 4/639 | (2006.01) |

(52) U.S. Cl.
CPC ............ C08F 110/02 (2013.01); C07C 2/32 (2013.01); C08F 4/025 (2013.01); C08F 4/6222 (2013.01); C08F 4/6226 (2013.01); C08F 4/69215 (2013.01); C08F 210/16 (2013.01); C07C 2/06 (2013.01); C08F 4/63912 (2013.01); C08F 4/63916 (2013.01); C08F 4/6592 (2013.01); C08F 4/65927 (2013.01); C08F 2420/02 (2013.01)

(58) Field of Classification Search
CPC ....... C07C 2/06; C07C 2/32; C08F 4/65927; C08F 4/65912; C08F 4/69215; C08F 210/02; C08F 110/02; C08F 210/16
See application file for complete search history.

(56) References Cited

U.S. PATENT DOCUMENTS

| | | |
|---|---|---|
| 4,071,673 A | 1/1978 | Hwang |
| 4,117,217 A | 9/1978 | Hwang |
| 4,284,527 A | 8/1981 | Pullukat et al. |
| 2005/0131262 A1 | 6/2005 | Dixon et al. |
| 2008/0021180 A1 | 1/2008 | Llatas et al. |

FOREIGN PATENT DOCUMENTS

| | | |
|---|---|---|
| CN | 1186813 A | 7/1998 |
| CN | 101080424 A | 11/2007 |
| CN | 101980783 A | 2/2011 |
| JP | 8-259618 A | 10/1996 |
| JP | 9-136912 A | 5/1997 |
| JP | 2000-281713 A | 10/2000 |
| JP | 2003-261534 A | 9/2003 |
| JP | 2007-533821 A | 11/2007 |
| JP | 4216431 B2 | 11/2008 |
| KR | 1998-064077 A | 10/1998 |
| KR | 2002-0063198 A | 8/2002 |
| KR | 10-0590136 B1 | 6/2006 |
| KR | 10-2007-0114696 A | 12/2007 |
| KR | 10-2011-0000559 A | 1/2011 |
| KR | 10-2012-0048468 A | 5/2012 |
| KR | 10-2012-0076156 A | 7/2012 |
| KR | 10-2012-0076965 A | 7/2012 |
| WO | 01/40322 A1 | 6/2001 |

OTHER PUBLICATIONS

Junwei Zhang et al. "Effect of Catalysts Supporting on Tandem Polymerization of Ethylene Stock in Synthesis of Ethylene-1-Hexene Copolymer" Ind. Eng. Chem. Res. 2008 pp. 5369-5375.
David S. McGuinness et al. "First Cr(III) SNS Complexes and Their Use as Highly Efficient Catalysts for the Trimerization of Ethylene to 1-Hexene" J. AM. Chemical Society, Apr. 15, 2003, pp. 5272-5273.
Wet-Roos De D et al: "Homogeneous Tandem Catalysis of Bis (2-Decylthioethyl)Amine-Chromium Trimerization Catalyst in Combination With Metallocene Catalysts", Macromolecules, American Chemical Society, US, vol. 37, No. 25, Dec. 14, 2004, pp. 9314-9320.

*Primary Examiner* — Caixia Lu
(74) *Attorney, Agent, or Firm* — Dentons US LLP

(57) ABSTRACT

A preparation method of a catalyst for polyolefin polymerization capable of polymerizing low-density polyethylene in a single reactor without separately injecting a comonomer to thereby prepare a final product with a low cost through a more simplified process, a catalyst obtained by the preparation method, and a preparation method of a polyolefin using the catalyst are provided.

9 Claims, No Drawings

PREPARATION METHOD OF CATALYST FOR POLYOLEFIN POLYMERIZATION AND PREPARATION METHOD OF POLYOLEFIN

This application is a National Stage Application of International Patent Application No. PCT/KR2013/003996, filed on May 8, 2013, and claims the benefit of Korean Patent Application Nos. 10-2013-0045011, filed on Apr. 23, 2013, in the Korean Intellectual Property Office, all of which are incorporated herein by reference in their entirety.

FIELD OF THE INVENTION

The present invention relates to a preparation method of a catalyst for polyolefin polymerization and a preparation method of a polyolefin, and more particularly, to a preparation method of a catalyst for polyolefin polymerization capable of polymerizing low-density polyethylene in a reactor without separately injecting a comonomer to thereby prepare a final product with a low cost by a more simplified process, and a preparation method of a polyolefin.

BACKGROUND OF THE INVENTION

Linear alpha-olefin, which is an important material used in a comonomer, a detergent, a lubricant, a plasticizer, or the like, is commercially widely used. Particularly, 1-hexene and 1-octene are mainly used as a comonomer for adjusting density of polyethylene when preparing linear low-density polyethylene (LLDPE).

In a process of preparing linear low-density polyethylene (LLDPE) according to the related art, a comonomer such as alpha-olefin, for example, 1-hexene and 1-octene, was copolymerized together with ethylene in order to form a branch in a polymer backbone to adjust density.

Therefore, in order to prepare LLDPE in which a content of the comonomer is high, there was a problem in that a cost of the comonomer was a large part of a manufacturing cost. In order to solve this problem, various methods have been attempted.

In addition, since an application field or a market size of alpha-olefin is different according to the kind thereof, commercially, a technology of selectively producing specific olefin is significantly important. Recently, research into a chromium catalyst technology for preparing 1-hexene or 1-octent with high selectivity through selective ethylene oligomerization has been mainly conducted.

As a commercial preparation method of 1-hexene or 1-octene according to the related art, there are the Shell higher olefin process (SHOP) process from Shell Chemical, the Ziegler process from Chevron Philips, and the like, and (C4~C10) alpha-olefin having wide molecular weight distribution may be prepared.

In addition, various researches into a technology of selectively preparing 1-hexene or 1-octene by an ethylene trimerization or tetramerization method using an organic metal catalyst have been conducted, but there was a disadvantage in that in the case of supporting the organic metal catalyst on a support such as silica, activity was significantly decreased (*J. Am. Chem. Soc.* 2003, 125, 5272, *Ind. Eng. Chem. Res.* 2008, 47, 5369).

DETAILED DESCRIPTION OF THE INVENTION

Technical Objectives

The present invention has been made in an effort to provide a preparation method of a catalyst for polyolefin polymerization capable of having high catalytic activity, securing high selectivity for an alpha-olefin, and polymerizing low density polyethylene in a single reactor without separately injecting a comonomer to thereby prepare a final product with a low cost through a more simplified process.

In addition, the present invention has been made in an effort to provide a preparation method of a polyolefin using a catalyst obtained by the preparation method of a catalyst for polyolefin polymerization.

Technical Solutions

There is provided a preparation method of a catalyst for polyolefin polymerization, including: supporting an organic chromium compound of the following Chemical Formula 1 on a support; supporting a cocatalyst containing a Group 13 metal on the support on which the organic chromium compound is supported; and supporting a metallocene catalyst on the support on which the organic chromium compound and the cocatalyst are supported.

[Chemical Formula 1]

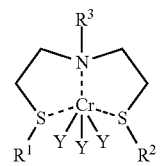

In Chemical Formula 1, $R^1$ and $R^2$ are the same or different and are each independently a hydrocarbyl group having 2 to 20 carbon atoms, containing a heteroatom selected from a group consisting of O, N, and P, $R^3$ is hydrogen or a hydrocarbyl group having 2 to 20 carbon atoms, containing a heteroatom selected from a group consisting of O, N, and P, and Y is a halogen, hydrogen, or a hydrocarbyl group having 1 to 4 carbon atoms.

And, there is provided a preparation method of a polyolefin including polymerizing an olefin monomer in the presence of a catalyst for polyolefin polymerization obtained by the preparation method for a catalyst for polyolefin polymerization.

Hereinafter, the preparation method of a catalyst for polyolefin polymerization and the preparation method of a polyolefin according to exemplary embodiments of the present invention will be described.

In the present specification, a polyolefin is used to mean all polymers of one kind of polyolefin monomer and copolymers of two kinds or more of olefin monomers.

According to an exemplary embodiment of the present invention, a preparation method of a catalyst for polyolefin polymerization is provided, including: supporting an organic chromium compound of Chemical Formula 1 on a support; supporting a cocatalyst containing a Group 13 metal on the support on which the organic chromium compound is supported; and supporting a metallocene catalyst on the support on which the organic chromium compound and the cocatalyst are supported.

In a general process of preparing a catalyst for polyolefin polymerization, a step of supporting a cocatalyst such as methyl aluminoxane (MAO), or the like, and then supporting a polymerization catalyst or an organic chromium compound on a support is performed. However, since an amount of the cocatalyst capable of being supported on silica is limited, a supporting amount of a metallocene catalyst or organic chromium compound to be subsequently supported is determined depending on an amount of the supported cocatalyst, and an activity of the polymerization catalyst such as the metallocene catalyst, or the like, may be decreased due to the organic chromium compound supported after the cocatalyst was supported.

In the case of various organic chromium catalysts according to the related art, at the time of a liquid phase reaction using methyl aluminoxane (hereinafter referred to as "MAO") or borate as the cocatalyst, 1-hexane may be prepared with high activity and selectivity, but in the case of supporting the catalyst on a support together with a cocatalyst, the activity was significantly decreased. Further, there was a limitation that in the case in which a previously known organic chromium compound was supported before the cocatalyst, the organic chromium compound did not have activity during a polyolefin polymerization process.

Therefore, it was difficult to develop a catalyst containing a cocatalyst, a metallocene catalyst for polyolefin polymerization, and an organic chromium catalyst increasing selectivity for a comonomer.

Therefore, the present inventors found through an experiment that in the case of using a catalyst prepared by the preparation method of a catalyst for polyolefin polymerization according to the exemplary embodiment, high selectivity for the comonomer such as 1-hexene or 1-octene injected in order to polymerize low-density polyethylene may be secured, and the low-density polyethylene may be polymerized in a reactor without separately injecting the comonomer, thereby completing the present invention.

Particularly, the present inventors confirmed that at the time of preparing a catalyst for olefin polymerization, even in the case of supporting the organic chromium compound of Chemical Formula 1 on a support and then supporting a cocatalyst containing a Group 13 metal and the metallocene catalyst, selectivity for a linear alpha-olefin may be secured at a high level, and an active site of the metallocene catalyst may be significantly increased, such that activity of a polymerization reaction catalyst may also be significantly improved.

More specifically, it was confirmed that in the case of using a different kind of organic chromium compound and the case of changing a supporting sequence of the organic chromium compound and the cocatalyst to prepare the catalyst for polyolefin polymerization, selectivity for a linear alpha-olefin such as 1-hexene and/or 1-octene and the catalytic activity were relatively low.

In addition, unlike a general preparation method of a catalyst for polyolefin polymerization, since the cocatalyst may be supported on the support after the organic chromium compound is supported on the support, an amount of the supported organic chromium compound may be adjusted. Therefore, the amount of the supported organic chromium compound may be adjusted in order to increase selectivity for a linear alpha-olefin such as 1-hexene or 1-octene, such that an olefin such as low-density polyethylene (PE) having various physical properties may be polymerized.

In the organic chromium compound of Chemical Formula 1 contained in the catalyst for polyolefin polymerization according to the above-mentioned exemplary embodiment, an alkoxy group may be introduced at a terminal of a ligand, such that solubility of the cocatalyst or metallocene catalyst in an organic solvent (for example, toluene, hexane, or the like) may be increased. In addition, the organic chromium compound of Chemical Formula 1 may be efficiently bound to the support to thereby be supported thereon due to a characteristic chemical structure thereof, and may maintain the activity thereof while being efficiently bound to the cocatalyst.

As described above, in Chemical Formula 1, $R^1$ and $R^2$ are the same or different and are each independently the hydrocarbyl group having 2 to 20 carbon atoms, containing a heteroatom selected from a group consisting of O, N, and P.

Further, in Chemical Formula 1, $R^1$ and $R^2$ each may be a hydrocarbyl group having 2 to 20 carbon atoms, containing a t-butoxy group at a terminal of an alkyl group.

In detail, $R^1$ and $R^2$ may each be a hydrocarbyl group having 2 to 20 carbon atoms, of which an alkoxy group such as a t-butoxy group, an iso-butoxy group, a sec-butoxy group, an iso-propoxy group, an n-propoxy group, an ethoxy group, and a methoxy group is bound to the terminal, and preferably, may be t-butoxy hexyl.

In Chemical Formula 1, $R^3$ may be hydrogen or the hydrocarbyl group having 2 to 20 carbon atoms, containing a heteroatom selected from a group consisting of O, N, and P, and Y may be a halogen, hydrogen, or the hydrocarbyl group having 1 to 4 carbon atoms.

Further, in Chemical Formula 1, $R^3$ may be hydrogen or a hydrocarbyl group having 2 to 20 carbon atoms, containing the t-butoxy group at the terminal of the alkyl group.

In detail, $R^3$ may be hydrogen or a hydrocarbyl group having 2 to 20 carbon atoms, containing an alkoxy group such as a t-butoxy group, an iso-butoxy group, a sec-butoxy group, an iso-propoxy group, an n-propoxy group, an ethoxy group, and a methoxy group at a terminal thereof.

In Chemical Formula 1, Y may be a halogen, hydrogen, or the hydrocarbyl group having 1 to 4 carbon atoms, preferably, a halogen or a methyl group, and more preferably, chlorine (Cl).

In Chemical Formula 1, chromium (Cr) may be coordinated with sulfur (S) and nitrogen (N).

Meanwhile, in the preparation method according to an exemplary embodiment of the present invention, after the supporting of the organic chromium compound of Chemical Formula 1 on the support and the supporting of the cocatalyst containing the Group 13 metal on the support on which the organic chromium compound is supported, the supporting of the metallocene catalyst on the support on which the organic chromium compound and the cocatalyst are supported may be further performed.

As the metallocene catalyst supported on (fixed to) the support on which the organic chromium compound and the cocatalyst are supported, a general metallocene catalyst known as capable of being used to synthesize a polyolefin resin may be used.

However, in order to secure high selectivity for a linear alpha-olefin and increase efficiency of a polymerization reaction, the metallocene catalyst may include one kind or more selected from a group consisting of compounds of Chemical Formulas 2 and 3.

[Chemical Formula 2]

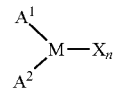

In Chemical Formula 2, $A^1$ and $A^2$ are the same or different and are each independently one kind of functional group selected from a group consisting of cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butyl methyl cyclopentadienyl, trimethylsilylcyclopentadienyl, indenyl, methylindenyl, ethylindenyl, isopropylindenyl, fluorenyl, methylfluorenyl, dimethylfluorenyl, ethylfluorenyl, and isopropylfluorenyl.

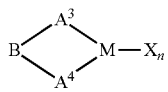

[Chemical Formula 3]

In Chemical Formula 3, $A^3$ and $A^4$ are the same or different and each are independently one kind of functional group selected from a group consisting of cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, (tert-butyl)(methyl)cyclopentadienyl, trimethylsilylcyclopentadienyl, indenyl, methylindenyl, ethylindenyl, isopropylindenyl, fluorenyl, methylfluorenyl, dimethylfluorenyl, ethylfluorenyl, isopropylfluorenyl, and —NR4—.

$R_4$ is hydrogen, a straight or branched alkyl group having 1 to 20 carbon atoms, a cycloalkyl group having 3 to 20 carbon atoms, or an alkylcycloalkyl group having 4 to 30 carbon atoms, substituted with at least one alkyl group having 1 to 10 carbon atoms.

B may be any one selected from a group consisting of an alkylene having 1 to 4 carbon atoms; an alkyl silicon or germanium having 1 to 4 carbon atoms; an alkyl phosphine or amine having 1 to 4 carbon atoms; an arylene group having 6 to 30 carbon atoms; an arylalkylene group having 6 to 30 carbon atoms; an alkylarylene group having 6 to 30 carbon atoms; and a functional group of the following Chemical Formula 31.

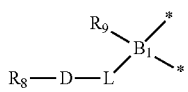

[Chemical Formula 31]

In Chemical Formula 31, $B_1$ may be silicon, germanium, phosphorus, nitrogen, boron, or aluminum, $R_9$ may be a straight or branched alkyl having 1 to 10 carbon atoms, $R_8$ may be hydrogen, or a straight or branched alkyl having 1 to 10 carbon atoms, D may be oxygen or sulfur, and L may be a straight or branched alkylene having 1 to 15 carbon atoms. * means a binding site.

In Chemical Formulas 2 and 3, M may be a Group 3 to 11 transition metal, more specifically, may be zirconium, titanium, or hafnium.

Further, in Chemical Formulas 2 and 3, X may be selected from a group consisting of an alkyl group having 1 to 20 carbon atoms, a cycloalkyl group having 3 to 20 carbon atoms, an alkylsilyl group having 1 to 20 carbon atoms, a silylalkyl group having 1 to 20 carbon atoms, an aryl group having 6 to 20 carbon atoms, an arylalkyl group having 7 to 20 carbon atoms, an alkylaryl group having 7 to 20 carbon atoms, an arylsilyl group having 6 to 20 carbon atoms, a silylaryl group having 6 to 20 carbon atoms, an alkoxy group having 1 to 20 carbon atoms, an alkylsiloxyl group having 1 to 20 carbon atoms, an aryloxy group having 6 to 20 carbon atoms, a halogen group, an amine group, and a tetrahydroborate group, and more specifically, X may be a chloride group, a trimethylsilylmethyl group, or a methyl group.

In addition, in Chemical Formulas 2 and 3, n is an integer of 1 to 5.

Meanwhile, a specific example of the metallocene catalyst of Chemical Formula 3 may be defined as follows.

In Chemical Formula 3, $A^3$ and $A^4$ may be the same or different and each may be cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, (tert-butyl)(methyl)cyclopentadienyl, trimethylsilylcyclopentadienyl, indenyl, methylindenyl, ethylindenyl, isopropylindenyl, fluorenyl, methylfluorenyl, dimethylfluorenyl, ethylfluorenyl, or isopropylfluorenyl.

Further, in Chemical Formula 3, $A^3$ may be —NR4—, and $A^4$ may be cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, (tert-butyl)(methyl)cyclopentadienyl, trimethylsilylcyclopentadienyl, indenyl, methylindenyl, ethylindenyl, isopropylindenyl, fluorenyl, methylfluorenyl, dimethylfluorenyl, ethylfluorenyl, or isopropylfluorenyl.

$R_4$ may be hydrogen or a straight or branched alkyl group having 1 to 20 carbon atoms, B may be the functional group of Chemical Formula 31, M may be zirconium, titanium, or hafnium, X may be the halogen group, and n may be 2.

In addition, the catalyst for polyolefin polymerization according to the above-mentioned exemplary embodiment may further contain the cocatalyst. This cocatalyst is not particularly limited as long as it is an organic metal compound containing a Group 13 metal and may be generally used in polymerizing olefin in the presence of a transition metal compound catalyst.

In detail, the cocatalyst may be one kind or more selected from a group consisting of compounds represented by Chemical Formulas 4 to 6, but the present invention is not limited thereto.

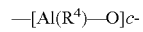  [Chemical Formula 4]

In Chemical Formula 4, $R^4(s)$ are the same or different and are each independently a halogen radical, a hydrocarbyl radical having 1 to 20 carbon atoms, or a halogen-substituted hydrocarbyl radical having 1 to 20 carbon atoms, and c is an integer of 2 or more.

  [Chemical Formula 5]

In Chemical Formula 5,

D is aluminum or boron, and $R^5$ is a hydrocarbyl having 1 to 20 carbon atoms, or a halogen-substituted hydrocarbyl having 1 to 20 carbon atoms.

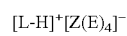  [Chemical Formula 6]

In Chemical Formula 6,

L is a neutral Lewis base, $[L-H]^+$ is a Bronsted acid, Z is boron or aluminum in a +3 oxidation state, and E(s) are each independently an aryl group having 6 to 20 carbon atoms or an alkyl group having 1 to 20 carbon atoms, in which one or more hydrogen atoms thereof are unsubstituted or substituted with a halogen, a hydrocarbyl having 1 to 20 carbon atoms, an alkoxy functional group, or a phenoxy functional group.

An example of the compound represented by Chemical Formula 4 may include methyl aluminoxane (MAO), ethyl aluminoxane, isobutyl aluminoxane, butyl aluminoxane, and the like.

An example of an alkyl metal compound represented by Chemical Formula 4 may include trimethylaluminum, triethylaluminum, triisobutylaluminum, tripropylaluminum, tributylaluminum, dimethylchloroaluminum, dimethyl isobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminummethoxide, dimethylaluminumethoxide, trimethyl boron, triethylboron, triisobutyl boron, tripropylboron, tributylboron, and the like.

An example of the compound represented by Chemical Formula 5 may include triethylammoniumtetraphenylboron, tributylammoniumtetraphenylboron, trimethylammoniumtetraphenylboron, tripropylammoniumtetraphenylboron, trimethylammoniumtetra(p-tolyl)boron, tripropylammoniumtetra(p-tolyl)boron, triethylammoniumtetra(o,p-dimethylphenyl)boron, trimethylammoniumtetra(o,p-dimethylphenyl)boron, tributylammoniumtetra(p-trifluoromethylphenyl) boron, trimethylammoniumtetra(p-trifluoromethylphenyl) boron, tributylammoniumtetrapentafluorophenyl boron, N,N-diethylaniliniumtetraphenylboron N,N-diethylaniliniumtetraphenylboron, N,N-diethylaniliniumtetrapentafluorophenylboron, diethylammoniumtetrapentafluorophenylboron, triphenylphosphoniumtetraphenylboron, trimethylphosphoniumtetraphenylboron, triethylammoniumtetraphenylaluminum, tributylammoniumtetraphenylaluminum, trimethylammoniumtetraphenylaluminum, tripropylammoniumtetraphenylaluminum, trimethylammoniumtetra(p-tolyl)aluminum, tripropylammoniumtetra(p-tolyl)aluminum, triethylammoniumtetra(o,p-dimethylphenyl)aluminum, tributylammoniumtetra(p-trifluoromethylphenyl)aluminum, trimethylammoniumtetra(p-trifluoromethyl phenyl)aluminum, tributylammoniumtetrapentafluorophenylaluminum, N,N-diethylaniliniumtetraphenylaluminum, N,N-diethylaniliniumtetrapentafluorophenylaluminum, diethylammoniumtetrapentafluorophenylaluminum, triphenylphosphoniumtetraphenylaluminum, trimethylphosphoniumtetraphenylaluminum, triphenylcarboniumtetraphenylboron, triphenylcarboniumtetraphenylaluminum, triphenylcarboniumtetra(p-trifluoromethylphenyl)boron, triphenylcarboniumtetrapentafluorophenylboron, and the like.

In the catalyst for polyolefin polymerization in which the organic chromium compound, the metallocene catalyst, and the cocatalyst are supported on the support as described above, a content of each component is not limited, but in order to increase selectivity for a linear alpha-olefin and olefin polymerization efficiency, 1 to 20 parts by weight of the organic chromium compound of Chemical Formula 1, 5 to 100 parts by weight of the cocatalyst, and 1 to 20 parts by weight of the metallocene catalyst may be supported, based on 100 parts by weight of the support.

The support may include any one selected from a group consisting of silica, silica-alumina, and silica-magnesia. The support may be dried at a high temperature and generally include an oxide component, a carbonate component, a sulfate component, or a nitrate component such as $Na_2O$, $K_2CO_3$, $BaSO_4$, and $Mg(NO_3)_2$.

The smaller the amount of a hydroxyl group (—OH) on a surface of the support, the better, but it is practically difficult to remove all of the hydroxyl groups. The amount of the hydroxyl group may be adjusted by a preparation method, preparation conditions, and drying conditions (temperature, time, a drying method, and the like) of the support, or the like, and may be preferably 0.1 to 10 mmol/g, more preferably, 0.1 to 1 mmol/g, and further more preferably, 0.1 to 0.5 mmol/g. In order to decrease side reactions by a small amount of the remaining hydroxyl group after drying, a support in which this hydroxyl group is chemically removed while maintaining a siloxane group having high reactivity of participating in the supporting may be used.

Meanwhile, according to another exemplary embodiment of the present invention, a preparation method of a polyolefin is provided, including polymerizing an olefin monomer in the presence of a catalyst for polyolefin polymerization obtained by the preparation method in the abovementioned exemplary embodiment.

As described above, the catalyst for polyolefin polymerization obtained by the preparation method in the abovementioned exemplary embodiment may contain the organic chromium compound capable of having high selectivity for a linear alpha-olefin and the metallocene catalyst capable of increasing polyolefin polymerization efficiency, such that olefins having various physical properties may be prepared using a single catalyst.

In detail, in the case of using the catalyst for polyolefin polymerization, high selectivity for a linear alpha-olefin may be secured, and an active site of the metallocene catalyst may be significantly increased, such that activity of the polymerization reaction catalyst may be also significantly improved. Further, in the case of using the catalyst for polyolefin polymerization, high selectivity for the comonomer such as 1-hexene or 1-octene injected in order to polymerize low-density polyethylene may be secured, the low-density polyethylene may be polymerized in a single reactor without separately injecting the comonomer, and a final product may be prepared with a low cost through a more simplified process.

An olefin monomer used in the preparation method of a polyolefin may include ethylene, and preferably, ethylene may be used alone.

A polyolefin provided according to the preparation method may be a low-density polyolefin.

In the preparation method of a polyolefin, generally used reaction conditions and reaction apparatus may be used without a particular limitation except for using the above-mentioned catalyst.

Advantageous Effect of the Invention

According to the present invention, the preparation method of a catalyst for polyolefin polymerization capable of having high catalytic activity, securing high selectivity for an alpha-olefin, and polymerizing low-density polyethylene in the single reactor without separately injecting the comonomer to thereby prepare a final product with the low cost through the more simplified process, the catalyst obtained by the preparation method, and the preparation method of a polyolefin using the catalyst may be provided.

In the case of using the obtained catalyst for polyolefin polymerization, polymerization of the polymer and preparation of the alpha-olefin may be simultaneously performed using one catalyst, such that the low-density polyolefin may be prepared in the single reactor by using a small amount of a comonomer or by using only ethylene without the comonomer.

DETAILED DESCRIPTION OF THE EMBODIMENTS

Hereinafter, actions and effects of the present invention will be described in more detail with reference to examples of the present invention. However, these examples are provided only for illustrative purpose, and do not limit a scope of the present invention.

PREPARATION EXAMPLE

Preparation of Organic Chromium Compound

1. Preparation Example 1

(1) Preparation of Tert-Butoxyhexane-1-Thiol

After 73.2 g of 1-tert-butoxy-6-chlorohexane (0.38 mol), 38 g of thiourea (0.5 mol), and 30 ml of distilled water were put into a 500 ml two-necked flask equipped with a condenser and refluxed at 120° C. for 5 hours, a temperature was cooled to room temperature, and 300 ml of a previously prepared aqueous solution of NaOH (30 g) was added thereto and refluxed at 110° C. for 14 hours. The reactant was cooled to room temperature, the formed organic layer was extracted with ether and dried over $MgSO_4$, and then the solvent was removed under reduced pressure, thereby obtaining 55.6 g of an oily product (6-tert-butoxyhexane-1-thiol, yield 76.9 mol %). Purity of the product confirmed through gas chromatography (GC) analysis was 97%, and results of proton nuclear magnetic resonance ($^1$H-NMR) spectroscopy were as follows.

$^1$H-NMR (500 MHz)(CDCl3) δ(ppm): 3.33(t, 2H), 2.53(t, 2H), 1.62(m, 2H), 1.52(m, 2H), 1.31-1.41(m, 4H), 1.18(s, 9H)

(2) Preparation of bis(2-(6-tert-butoxyhexylthio)ethyl)amine

After 1 g of NaOH (25 mmol) was injected into 50 ml of an ethanol solution of bis(2-chloroethyl)amine hydrochloride salt (4.46 g, 25 mmol) and stirred at room temperature for 10 minutes, 75 ml of an ethanol solution of the above prepared tert-butoxyhexane-1-thiol (9.52 g, 50 mmol) and NaOH (2 g, 50 mmol) was added thereto and stirred overnight at room temperature. After drying a filtrate obtained by filtering the reactant, a filtrate obtained by filtering and removing a solid that was not dissolved in ether again was dried, thereby obtaining 10.7 g of an oily product (bis(2-(6-tert-butoxyhexylthio)ethyl)amine, yield 95 mol %).

Results of $^1$H-NMR were as follows.

$^1$H-NMR (500 MHz)(CDCl3) δ(ppm): 3.29(t, 4H), 2.79(t, 4H), 2.64(t, 4H), 2.48(t, 4H), 1.56(m, 4H), 1.48(m, 4H), 1.31-1.39(m, 8H), 1.15(s, 18H)

(3) Preparation of [bis(2-(6-tert-butoxyhexylthio)ethyl)amine]$CrCl_3$ complex $CrCl_3(THF)_3$ (0.2 mmol) and 10 ml of purified tetrahydrofuran (THF) were injected into a Schlenk flask under an argon atmosphere. The above-prepared bis(2-(6-tert-butoxyhexylthio)ethyl)amine (0.2 mmol) and 10 mL of purified THF were also prepared in a Schlenk flask under an argon atmosphere. Each of the solutions was cooled to −5° C., and the ligand solution was slowly injected into the $CrCl_3(THF)_3$ solution using a cannula. The color of the solution was slowly changed from purple to green, and the temperature was slowly raised to room temperature. The mixed solution was stirred overnight. The solvent of the reactance was removed under reduced pressure, and the obtained sticky dark green solid was dissolved in 50 ml of purified toluene, thereby preparing a [bis(2-(6-tert-butoxyhexylthio)ethyl)amine]$CrCl_3$ complex.

2. Preparation Example 2

An organic chromium compound was synthesized by the same method as in Preparation Example 1, except for using dodecane-1-thiol instead of tert-butoxyhexane-1-thiol in Preparation Example 1.

A structure of the organic chromium compounds obtained the above Preparation Examples is as shown in the following Chemical Formula 1 and Table 1.

[Chemical Formula 1]

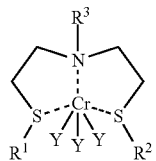

TABLE 1

| | $R_1$ | $R_2$ | $R_3$ | Y |
|---|---|---|---|---|
| Preparation Example 1 | t-butoxyhexyl group | t-butoxyhexyl group | hydrogen | Cl |
| Preparation Example 2 | Dodecyl | Dodecyl | hydrogen | Cl |

Example 1 and Comparative Examples 1 to 3

Preparation of Supported Catalyst and Synthesis of Linear Alpha-Olefin

1. Example 1

(1) Preparation of Supported Catalyst

Pressure in a 500 ml reactor was reduced to vacuum, and argon gas was used to provide an inert atmosphere in the reactor. Then, 100 ml of purified toluene was filled therein and 10 g of spherical silica [dehydrated under vacuum at 200° C. for 2 hours and having an average particle size of 30 μm] was added to the reactor using Schlenk technology.

Thereafter, a toluene diluted solution (organic chromium compound: 1.0 mmol) of 100 ml of toluene and the organic chromium compound obtained in Preparation Example 1 was added to the reactor and stirred at 40° C. and 200 rpm for 2 hours, followed by removal of the filtrate after 30 minutes.

Then, after 70 ml of 10% MAO toluene solution was added to the reactor and stirred at 80° C. and 200 rpm for 12 hours, the temperature was cooled to 40° C., and the stirring was stopped. 30 minutes after completion of the stirring, a toluene filtrate was removed except for the precipitated silica. The slurry remaining in the reactor was vacuum-dried, such that a supported catalyst E1 was prepared, and stored in a glove box.

(2) Synthesis of Linear Alpha-Olefin

A 2 L reactor was vacuum-dried, and argon gas was used to provide an inert atmosphere in the reactor. Then, 1 L of hexane and 1 ml of a hexane solution of triethylaluminum (1 M) were put into the reactor, and the temperature of the reactor was adjusted to 70° C.

Then, a slurry obtained by weighing 200 mg of the prepared supported catalyst in a 50 ml glass vessel and adding 40 ml of purified hexane thereto was delivered to a sample port connected to the reactor using a cannula. The catalyst slurry was injected into the reactor while being washed with 0.2 L of hexane. Next, after ethylene (40 bar) was applied to the reactor and saturated in the reactor for 1 minute, the stirring was performed at 500 rpm and a reaction was carried out for 1 hour. After the reaction was completed, the stirring was stopped, the reactor was cooled to room temperature, and the remaining ethylene gas was vented.

The reactor was opened and a polymerization solution was extracted, such that a composition of an organic layer was confirmed using gas chromatography-mass spectroscopy (GC-MS)/MS, and GC area % in which hexane corresponding to the reaction solution was removed was measured using a gas chromatography-flame ionization detector (GC-FID). In addition, after the reaction solution was filtered and dried so as to have a solid powder, an amount of the produced linear alpha-olefin was measured.

The measurement results are shown in the following Table 2.

2. Comparative Example 1

(1) Preparation of Supported Catalyst

A supported catalyst CE1 was prepared by the same method in Example 1, except for using a toluene diluted solution (organic chromium compound: 1.0 mmol) of the organic chromium compound obtained in Preparation Example 2 instead of the toluene diluted solution (organic chromium compound: 1.0 mmol) of the organic chromium compound obtained in Preparation Example 1.

(2) Synthesis of Linear Alpha-Olefin

A linear alpha-olefin was synthesized by the same method in Example 1, except for using the prepared supported catalyst CE1 instead of the supported catalyst E1, and then analysis was performed thereon.

3. Comparative Example 2

(1) Preparation of Supported Catalyst

Pressure in a 500 ml reactor was reduced to vacuum, and argon gas was used to provide an inert atmosphere in the reactor. Then, 100 ml of purified toluene was filled therein and 10 g of spherical silica [dehydrated under vacuum at 200° C. for 2 hours and having an average particle size of 30 μm] was added thereto using Schlenk technology.

Then, after 70 ml of a 10% MAO toluene solution was added to the reactor and stirred at 80° C. and 200 rpm for 12 hours, the temperature was cooled to 40° C., and the stirring was stopped. 30 minutes after completion of the stirring, toluene filtrate was removed except for the precipitated silica.

Thereafter, a toluene diluted solution (organic chromium compound: 1.0 mmol) of the 100 ml of toluene and the organic chromium compound obtained in Preparation Example 2 was added to the reactor and stirred at 40° C. and 200 rpm for 2 hours, followed by removal of the filtrate after 30 minutes. The slurry remaining in the reactor was vacuum-dried, such that a supported catalyst CE1 was prepared, and stored in a glove box.

(2) Synthesis of Linear Alpha-Olefin

A linear alpha-olefin was synthesized by the same method in Example 1, except for using the prepared supported catalyst CE2 instead of the supported catalyst E1, and then analysis was performed thereon.

4. Comparative Example 3

(1) Preparation of Supported Catalyst

A supported catalyst CE3 was prepared by the same method in Comparative Example 2, except for using the toluene diluted solution (organic chromium compound: 1.0 mmol) of the organic chromium compound obtained in Preparation Example 1 instead of the toluene diluted solution (organic chromium compound: 1.0 mmol) of the organic chromium compound obtained in Preparation Example 2.

(2) Synthesis of Linear Alpha-Olefin

A linear alpha-olefin was synthesized by the same method in Example 1, except for using the prepared supported catalyst CE3 instead of the supported catalyst E1, and then analysis was performed thereon.

TABLE 2

Synthesis Results of Example 1 and Comparative Examples 1 to 3

| | Hexene Selectivity (GC area %) | Octene Selectivity (GC area %) | Polyethylene (wt %) | Activity [g/g(Cr)]/hr |
|---|---|---|---|---|
| Example 1 | 89.6 | 10.4 | 3 | 6731 |
| Comparative Example 1 | — | — | trace | 0 |
| Comparative Example 2 | 98.1 | 1.9 | 3 | 3462 |
| Comparative Example 3 | 93.1 | 6.9 | 4 | 6538 |

As shown in Table 2, it was confirmed that in Example 1 in which the supported catalyst prepared in Preparation Example 1 was used, octene selectivity was 10 GC area % or more and a high catalytic activity was secured, such that polyethylene may be synthesized.

On the contrary, it was confirmed that in the case of Comparative Example 1 in which the supported catalyst prepared by supporting the organic chromium compound of Preparation Example 2 before the MAO cocatalyst was used, at the time of injecting the ethylene monomer, a polymerization reaction could not be performed.

Further, it was confirmed that in the case of Comparative Example 2 in which the catalyst prepared by supporting the organic chromium compound of Preparation Example 2 after supporting the MAO cocatalyst on the silica support was used, octene selectivity was significantly decreased as compared to Example 1, and the catalytic activity was only about 50% of that in Example 1.

In addition, it was confirmed that in the case of Comparative Example 3 in which the catalyst prepared by supporting the organic chromium compound of Preparation Example 1 after supporting the MAO cocatalyst on the silica support was used, the catalytic activity was secured to some degree, but octene selectivity was low as compared to Example 1.

Examples 2 to 4 and Comparative Examples 4 to 11

Preparation of Organic Chromium/Metallocene Hybrid-Supported Catalyst and Synthesis of Polyolefin In the following Examples 2 and 3 and Comparative Examples 4 to 10, (tert-Bu-O—$(CH_2)_6$)MeSi(9-$C_{13}H_9$)$_2$ZrCl$_2$ was used as the following polymerization catalyst A.

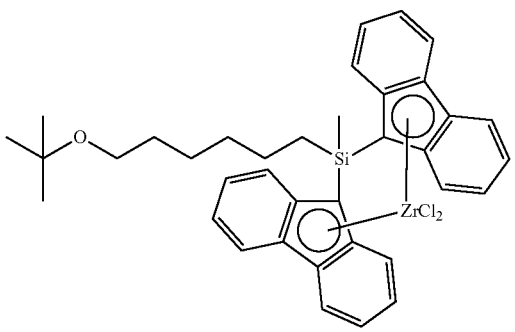

In addition, [(tert-Bu-O—(CH$_2$)$_6$)MeSi(C$_5$Me$_4$)(NCMe$_3$)]TiCl$_2$ was used as the following polymerization catalyst B.

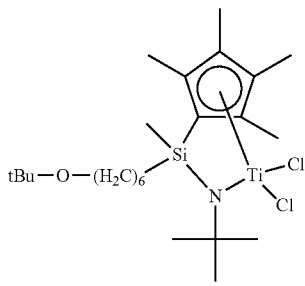

1. Example 2

(1) Preparation of Organic Chromium/Metallocene Hybrid-Supported Catalyst

Pressure in a 500 ml reactor was reduced to vacuum, and argon gas was used to provide an inert atmosphere in the reactor. Then, 100 ml of purified toluene was filled therein and 10 g of spherical silica [dehydrated under vacuum at 200° C. for 2 hours and having an average particle size of 30 μm] was added thereto using Schlenk technology.

Thereafter, a toluene diluted solution (organic chromium compound: 1.0 mmol) of the 100 ml of toluene and the organic chromium compound obtained in Preparation Example 1 was added to the reactor and stirred at 40° C. and 200 rpm for 2 hours, followed by removal of the filtrate after 30 minutes.

Then, after 70 ml of a 10% MAO toluene solution was added to the reactor and stirred at 80° C. and 200 rpm for 12 hours, the temperature was cooled to 40° C., and the stirring was stopped. 30 minutes after completion of the stirring, toluene filtrate was removed except for the precipitated silica.

In addition, 100 ml of toluene solution (5 mmol/L) in which the polymerization catalyst A (0.5 mmol) was dissolved was added to the reactor and stirred at 40° C. and 200 rpm for 2 hours. 30 minutes after completion of the stirring, the filtrate was removed, and the slurry remaining in the reactor was vacuum-dried, such that a metallocene supported catalyst E2 was prepared, and stored in a glove box.

(2) Synthesis of Polyolefin

A 2 L reactor was vacuum-dried, and argon gas was used to provide an inert atmosphere in the reactor. Then, 1 L of hexane and 1 ml of a hexane solution of triethylaluminum (1 M) were put into the reactor, and the temperature of the reactor was adjusted to 70° C.

Then, a slurry obtained by weighing 30 mg of the prepared supported catalyst in a 50 ml glass vessel and adding 40 ml of purified hexane thereto was delivered to a sample port connected to the reactor using a cannula.

The catalyst slurry was injected into the reactor while being washed with 0.2 L of hexane. Next, after ethylene (40 bar) was applied to the reactor and saturated in the reactor for 1 minute, the stirring was performed at 500 rpm and a reaction was carried out for 1 hour. After the reaction was completed, the stirring was stopped, the reactor was cooled to room temperature, and the remaining ethylene gas was vented.

The reactor was opened, and the produced polyethylene (PE) resin was filtered and dried. Physical properties of the PE resin were analyzed, and the results are shown in the following Table 3.

2. Example 3

(1) Preparation of Organic Chromium/Metallocene Hybrid-Supported Catalyst

A metallocene supported catalyst E3 was prepared by the same method in Example 2, except for using the polymerization catalyst B instead of the polymerization catalyst A.

(2) Synthesis of Polyolefin

A polyolefin was synthesized by the same method in Example 2, except for using the prepared metallocene supported catalyst E3 instead of the metallocene supported catalyst E2, and then analysis was performed thereon.

3. Example 4

(1) Preparation of Organic Chromium/Metallocene Hybrid-Supported Catalyst

A metallocene supported catalyst E3 was prepared by the same method in Example 2, except for using the polymerization catalyst B instead of the polymerization catalyst A.

(2) Synthesis of Polyolefin

A polyolefin was synthesized by the same method in Example 2, except for using the prepared metallocene supported catalyst E3 instead of the metallocene supported catalyst E2 and further adding 20 ml of 1-hexene during a reaction process, and then analysis was performed thereon.

4. Comparative Example 4

(1) Preparation of Organic Chromium/Metallocene Hybrid-Supported Catalyst

Pressure in a 500 ml reactor was reduced to vacuum, and argon gas was used to provide an inert atmosphere in the reactor. Then, 100 ml of purified toluene was filled therein and 10 g of spherical silica [dehydrated under vacuum at 200° C. for 2 hours and having an average particle size of 30 μm] was added thereto using Schlenk technology.

Then, after 70 ml of 10% MAO toluene solution was added to the reactor and stirred at 80° C. and 200 rpm for 12 hours, the temperature was cooled to 40° C., and the stirring was stopped. 30 minutes after completion of the stirring, toluene filtrate was removed except for the precipitated silica.

Thereafter, a toluene diluted solution (organic chromium compound: 1.0 mmol) of the 100 ml of toluene and the organic chromium compound obtained in Preparation Example 2 was added to the reactor and stirred at 40° C. and 200 rpm for 2 hours, followed by removal of the filtrate after 30 minutes.

In addition, 100 ml of a toluene solution (5 mmol/L) in which the polymerization catalyst A (0.5 mmol) was dissolved was added to the reactor and stirred at 40° C. and 200 rpm for 2 hours. 30 minutes after completion of the stirring, the filtrate was removed, and the slurry remaining in the reactor was vacuum-dried, such that a metallocene supported catalyst CE4 was prepared, and stored in a glove box.

(2) Synthesis of Polyolefin

A polyolefin was synthesized by the same method in Example 2, except for using the prepared metallocene supported catalyst CE4 instead of the metallocene supported catalyst E2, and then analysis was performed thereon.

5. Comparative Example 5

(1) Preparation of Organic Chromium/Metallocene Hybrid-Supported Catalyst

A metallocene supported catalyst CE5 was prepared by the same method in Comparative Example 4, except for using the toluene diluted solution (organic chromium compound: 1.0 mmol) of the organic chromium compound obtained in Preparation Example 1 instead of the toluene diluted solution (organic chromium compound: 1.0 mmol) of the organic chromium compound obtained in Preparation Example 2.

(2) Synthesis of Polyolefin

A polyolefin was synthesized by the same method in Example 2 except for using the prepared metallocene supported catalyst CE5 instead of the metallocene supported catalyst E2, and then analysis was performed thereon.

6. Comparative Example 6

(1) Preparation of Metallocene Supported Catalyst

Pressure in a 500 ml reactor was reduced to vacuum, and argon gas was used to provide an inert atmosphere in the reactor. Then, 100 ml of purified toluene was filled therein and 10 g of spherical silica [dehydrated under vacuum at 200° C. for 2 hours and having an average particle size of 30 µm] was added thereto using Schlenk technology.

Then, after 70 ml of 10% MAO toluene solution was added to the reactor and stirred at 80° C. and 200 rpm for 12 hours, the temperature was cooled to 40° C., and the stirring was stopped. 30 minutes after completion of the stirring, toluene filtrate was removed except for the precipitated silica.

Thereafter, 100 ml of toluene solution (5 mmol/L) in which the polymerization catalyst A (0.5 mmol) was dissolved was added to the reactor and stirred at 40° C. and 200 rpm for 2 hours. 30 minutes after completion of the stirring, the filtrate was removed, and the slurry remaining in the reactor was vacuum-dried, such that a metallocene supported catalyst CE6 was prepared, and stored in a glove box.

(2) Synthesis of Polyolefin

A polyolefin was synthesized by the same method in Example 2, except for using the prepared metallocene supported catalyst CE6 instead of the metallocene supported catalyst E2, and then analysis was performed thereon.

7. Comparative Example 7

A polyolefin was synthesized by the same method in Example 2, except for using the prepared metallocene supported catalyst CE6 instead of the metallocene supported catalyst E2 and further adding 20 ml of 1-hexene during a reaction process, and then analysis was performed thereon.

8. Comparative Example 8

(1) Preparation of Metallocene Supported Catalyst

A supported catalyst CE8 was prepared by the same method in Example 2, except for using the toluene diluted solution (organic chromium compound: 1.0 mmol) of the organic chromium compound obtained in Preparation Example 2 instead of the toluene diluted solution (organic chromium compound: 1.0 mmol) of the organic chromium compound obtained in Preparation Example 1.

(2) Synthesis of Polyolefin

A polyolefin was synthesized by the same method in Example 2, except for using the prepared metallocene supported catalyst CE8 instead of the metallocene supported catalyst E2, and then analysis was performed thereon.

9. Comparative Example 9

(1) Preparation of Metallocene Supported Catalyst

A metallocene supported catalyst CE9 was prepared by the same method in Comparative Example 5, except for using the polymerization catalyst B (0.5 mmol) instead of the polymerization catalyst A (0.5 mmol).

(2) Synthesis of Polyolefin

A polyolefin was synthesized by the same method in Example 2, except for using the prepared metallocene supported catalyst CE9 instead of the metallocene supported catalyst E2, and then analysis was performed thereon.

10. Comparative Example 10

(1) Preparation of Metallocene Supported Catalyst

A metallocene supported catalyst CE9 was prepared by the same method in Comparative Example 6, except for using the polymerization catalyst B (0.5 mmol) instead of the polymerization catalyst A (0.5 mmol).

(2) Synthesis of Polyolefin

A polyolefin was synthesized by the same method in Example 2, except for using the prepared metallocene supported catalyst CE10 instead of the metallocene supported catalyst E2, and then analysis was performed thereon.

11. Comparative Example 11

(1) Preparation of Metallocene Supported Catalyst

A metallocene supported catalyst CE11 was prepared by the same method in Comparative Example 6, except for using the polymerization catalyst B (0.5 mmol) instead of the polymerization catalyst A (0.5 mmol).

(2) Synthesis of Polyolefin

A polyolefin was synthesized by the same method in Example 2, except for using the prepared metallocene supported catalyst CE10 instead of the metallocene supported catalyst E2 and further adding 20 ml of 1-hexene during a reaction process, and then analysis was performed thereon.

TABLE 3

Synthesis Results of Polyolefin in Examples 2 to 4 and Comparative Examples 4 to 11

| | Activity [Kg/g(Supported Catalyst)]/hr | Melting Point (° C.) | Content of 1-Hexene (wt %) | Supporting Sequence | Whether or Not 1-Hexene was Added |
|---|---|---|---|---|---|
| Example 2 | 5.9 | 126.8 | 2.29 | Support-T1-MAO-Polymerization A | |
| Example 3 | 3.5 | 126.9 | 2.42 | Support-T1-MAO-Polymerization B | |
| Example 4 | 3.6 | 124.2 | 5.13 | Support-T1-MAO-Polymerization B | 20 ml |
| Comparative Example 4 | 2.1 | 131.7 | 0.55 | Support-MAO-T2-Polymerization A | |
| Comparative Example 5 | 5.9 | 128.8 | 1.93 | Support-MAO-T1-Polymerization A | |
| Comparative Example 6 | 5.6 | 133.2 | 0.10 | Support-MAO-Polymerization A | |
| Comparative Example 7 | 5.8 | 127.0 | 2.36 | Support-MAO-Polymerization A | 20 ml |
| Comparative Example 8 | 2.6 | 130.9 | 0.10 | Support-T2-MAO-Polymerization A | |
| Comparative Example 9 | 1.0 | 131.8 | 0.55 | Support-MAO-T1-Polymerization B | |
| Comparative Example 10 | 3.5 | 132.0 | 0.00 | Support-MAO-Polymerization B | |
| Comparative Example 11 | 4.0 | 126.4 | 2.78 | Support-MAO-Polymerization B | 20 ml |

1) In Table 3, T1 indicates the organic chromium compound prepared in Preparation Example 1, and T2 indicates the organic chromium compound prepared in Preparation Example 2. Polymerization A and Polymerization B mean the above-mentioned polymerization catalysts A and B, respectively.

2) The activity means a ratio of the obtained polymer to the amount of the supported catalyst after polymerization for 1 hour.

3) Measuring Method of Melting Point.

After the temperature was raised to 200° C. at a rate of 20° C./min in a state in which an equilibration was maintained at a temperature of 30° C. using a differential scanning calorimeter (DSC, TA instruments, DSC2920 model), the temperature was maintained for 5 minutes, such that thermal history of the copolymer sample was eliminated. After the temperature was lowered again to 10° C. at a rate of 10° C./min, an endothermic peak was confirmed while raising the temperature at a rate of 10° C./min, thereby measuring the melting point.

4) Content of 1-hexene

In $^1$H NMR data of the synthesized polyolefin, $CH_3$, $CH_2$, and CH peaks were quantified, and the content of 1-hexene was measured, considering that $CH_3$ was derived from 1-hexene.

As shown in Table 3, it was confirmed that in Examples 2 to 4, a high catalytic activity was secured and the content of 1-hexene contained in the synthesized polyolefin was relatively high.

Particularly, in Examples 2 and 3, low-density polyethylene may be polymerized with high efficiency without injecting a comonomer such as 1-hexene, or the like, and the content of 1-hexene in the synthesized resin may be increased at a level similar to or more than a level in Comparative Examples 7 and 11 in which 1-hexene was additionally added. In addition, as shown in the result of Example 4, in the case of additionally adding 1-hexene in the polymerization process, the content of 1-hexene in the synthesized resin may be significantly increased.

Therefore, in the examples, polymerization of the polymer and preparation of alpha-olefin may be simultaneously performed using one catalyst, such that a low-density polyolefin may be synthesized in the single reactor by using a small amount of the comonomer or by using only ethylene without the comonomer.

What is claimed is:

1. A preparation method of a catalyst for polyolefin polymerization, the preparation method comprising:
supporting an organic chromium compound of the following Chemical Formula 1 on a support including one or more selected from a group consisting of silicia, silica-alumina, and silica-magnesia;
supporting a cocatalyst containing a Group 13 metal on the support on which the organic chromium compound is supported; and
supporting a metallocene catalyst on the support on which the organic chromium compound and the cocatalyst are supported:

[Chemical Formula 1]

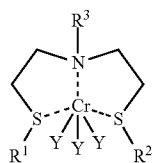

in Chemical Formula 1,
$R^1$ and $R^2$ are the same or different and are each independently a hydrocarbyl group having 2 to 20 carbon atoms, containing a heteroatom selected from a group consisting of O, N, and P,
$R^3$ is hydrogen or a hydrocarbyl group having 2 to 20 carbon atoms, containing a heteroatom selected from a group consisting of O, N, and P, and
Y is a halogen, hydrogen, or a hydrocarbyl group having 1 to 4 carbon atoms.

2. The preparation method of claim 1, wherein in Chemical Formula 1, $R^1$ and $R^2$ are each a hydrocarbyl group having 2 to 20 carbon atoms, and containing a t-butoxy group at a terminal of an alkyl group.

3. The preparation method of claim 1, wherein in Chemical Formula 1, $R^3$ is hydrogen or a hydrocarbyl group having 2 to 20 carbon atoms, and containing a t-butoxy group at a terminal of an alkyl group.

4. The preparation method of claim 1, wherein in Chemical Formula 1, Y is a halogen or a methyl group.

5. The preparation method of claim 1, wherein the metallocene catalyst includes one kind or more selected from a group consisting of compounds of Chemical Formulas 2 and 3:

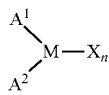
[Chemical Formula 2]

in Chemical Formula 2,
$A^1$ and $A^2$ are the same or different and are each independently one kind of functional group selected from a group consisting of cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, (tert-butyl)(methyl)cyclopentadienyl, trimethylsilylcyclopentadienyl, indenyl, methylindenyl, ethylindenyl, isopropylindenyl, fluorenyl, methylfluorenyl, dimethylfluorenyl, ethylfluorenyl, and isopropylfluorenyl,

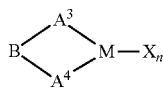
[Chemical Formula 3]

in Chemical Formula 3,
$A^3$ and $A^4$ are the same or different and are each independently one kind of functional group selected from a group consisting of cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, (tert-butyl)(methyl)cyclopentadienyl, trimethylsilylcyclopentadienyl, indenyl, methylindenyl, ethylindenyl, isopropylindenyl, fluorenyl, methylfluorenyl, dimethylfluorenyl, ethylfluorenyl, isopropylfluorenyl, and —$NR_4$—,
$R_4$ is hydrogen, a straight or branched alkyl group having 1 to 20 carbon atoms, a cycloalkyl group having 3 to 20 carbon atoms, or an alkylcycloalkyl group having 4 to 30 carbon atom, substituted with at least one alkyl group having 1 to 10 carbon atoms, and
B is any one selected from a group consisting of an alkylene having 1 to 4 carbon atoms; an alkyl silicon or germanium having 1 to 4 carbon atoms; an alkyl phosphine or amine having 1 to 4 carbon atoms; an arylene group having 6 to 30 carbon atoms; an arylalkylene group having 6 to 30 carbon atoms; an alkylarylene group having 6 to 30 carbon atoms; and a functional group of the following Chemical Formula 31,

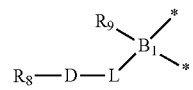
[Chemical Formula 31]

in Chemical Formula 31,
$B_1$ is silicon, germanium, phosphorus, nitrogen, boron, or aluminum,
$R_9$ is a straight or branched alkyl having 1 to 10 carbon atoms,
$R_8$ is hydrogen or a straight or branched alkyl having 1 to 10 carbon atoms,
D is oxygen or sulfur,
L is a straight or branched alkyl having 1 to 15 carbon atoms,
* means a binding site,
in Chemical Formulas 2 and 3,
M is a Group 3 to 11 transition metal,
X is selected from a group consisting of an alkyl group having 1 to 20 carbon atoms, a cycloalkyl group having 3 to 20 carbon atoms, an alkylsilyl group having 1 to 20 carbon atoms, a silylalkyl group having 1 to 20 carbon atoms, an aryl group having 6 to 20 carbon atoms, an arylalkyl group having 7 to 20 carbon atoms, an alkylaryl group having 7 to 20 carbon atoms, an arylsilyl group having 6 to 20 carbon atoms, a silylaryl group having 6 to 20 carbon atoms, an alkoxy group having 1 to 20 carbon atoms, an alkylsiloxyl group having 1 to 20 carbon atoms, an aryloxy group having 6 to 20 carbon atoms, a halogen group, an amine group, and a tetrahydroborate group, and n is an integer of 1 to 5.

6. The preparation method of claim 5, wherein in Chemical Formula 3,
$A^3$ and $A^4$ are the same or different and are each cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, tert-butyl methylcyclopentadienyl, trimethylsilylcyclopentadienyl, indenyl, methylindenyl, ethylindenyl, isopropylindenyl, fluorenyl, methylfluorenyl, dimethylfluorenyl, ethylfluorenyl, or isopropylfluorenyl,
$A^3$ is —$NR_4$—, and $A^4$ is cyclopentadienyl, methylcyclopentadienyl, dimethylcyclopentadienyl, tetramethylcyclopentadienyl, pentamethylcyclopentadienyl, butylcyclopentadienyl, sec-butylcyclopentadienyl, (tert-butyl)(methyl)cyclopentadienyl, trimethylsilylcyclopentadienyl, indenyl, methylindenyl, ethylindenyl, isopropylindenyl, fluorenyl, methylfluorenyl, dimethylfluorenyl, ethylfluorenyl, or isopropylfluorenyl,
$R_4$ is hydrogen or a straight or branched alkyl having 1 to 20 carbon atoms,
B is the functional group of Chemical Formula 31,
M is zirconium, titanium, or hafnium,
X is a halogen group, and n is 2.

7. The preparation method of claim 1, wherein the cocatalyst is one kind or more selected from a group consisting of compounds of Chemical Formulas 4 to 6:

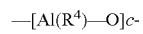 [Chemical Formula 4]

in Chemical Formula 4, $R^4$(s) are the same or different and are each independently a halogen radical, a hydrocarbyl radical having 1 to 20 carbon atoms, or a halogen-substituted hydrocarbyl radical having 1 to 20 carbon atoms, and c is an integer of 2 or more, $$D(R^5)_3 \qquad \text{[Chemical Formula 5]}$$

in Chemical Formula 5,

D is aluminum or boron, and $R^5$ is a hydrocarbyl having 1 to 20 carbon atoms, or a halogen-substituted hydrocarbyl having 1 to 20 carbon atoms, $$[L\text{-}H]^+[Z(E)_4]^- \qquad \text{[Chemical Formula 6]}$$

in Chemical Formula 6,

L is a neutral Lewis base, $[L\text{-}H]^+$ is a Bronsted acid,

Z is boron or aluminum in a +3 oxidation state, and

E(s) are each independently an aryl group having 6 to 20 carbon atoms or an alkyl group having 1 to 20 carbon atoms, in which one or more hydrogen atoms thereof are unsubstituted or substituted with a halogen, a hydrocarbyl having 1 to 20 carbon atoms, an alkoxy functional group, or a phenoxy functional group.

8. The preparation method of claim 1, wherein based on 100 parts by weight of the support,
- 1 to 20 parts by weight of the organic chromium compound of Chemical Formula 1;
- 5 to 100 parts by weight of the cocatalyst; and
- 1 to 20 parts by weight of the metallocene catalyst are supported.

9. A preparation method of a polyolefin, comprising polymerizing an olefin monomer in the presence of the catalyst for polyolefin polymerization obtained by the preparation method of claim 1.

* * * * *